United States Patent [19]

Bethge et al.

[11] 4,416,828

[45] Nov. 22, 1983

[54] PROCESS FOR THE RESOLUTION OF THE RACEMATE S-(CARBOXYMETHYL)-(RS)-CYSTEINE (A)

[75] Inventors: Horst Bethge; Axel Kleemann, both of Hanau; Jürgen Martens, Alzenau, all of Fed. Rep. of Germany

[73] Assignee: Degussa Aktiengesellschaft, Frankfurt, Fed. Rep. of Germany

[21] Appl. No.: 411,324

[22] Filed: Aug. 25, 1982

[30] Foreign Application Priority Data

Aug. 28, 1981 [DE] Fed. Rep. of Germany ....... 3134042

[51] Int. Cl.$^3$ .............................................. C07C 99/12
[52] U.S. Cl. ............................... 260/501.12; 562/401; 564/355
[58] Field of Search ................... 260/501.12; 562/401; 564/355

[56] References Cited

U.S. PATENT DOCUMENTS

| | | | |
|---|---|---|---|
| 3,808,268 | 4/1974 | Rambacker et al. | 562/401 |
| 4,224,457 | 9/1980 | Itao et al. | 562/401 |
| 4,245,117 | 1/1981 | Scherberich | 562/554 |

FOREIGN PATENT DOCUMENTS

| | | | |
|---|---|---|---|
| 1795021 | 12/1971 | Fed. Rep. of Germany | 562/554 |
| 2545748 | 4/1978 | Fed. Rep. of Germany | 562/554 |
| 2653332 | 6/1978 | Fed. Rep. of Germany | 562/554 |
| 2147812 | 4/1973 | France | 562/554 |

OTHER PUBLICATIONS

Vigneaud, J. Amer. Chem. Soc. vol. 52, pp. 4500–4504 (1930).
Armstrong, J. Org. Chem., vol. 16, pp. 749–753 (1951).
Org. Syntheses, vol. 5 (1925), pp. 39–41.

*Primary Examiner*—James H. Reamer
*Attorney, Agent, or Firm*—Cushman, Darby & Cushman

[57] ABSTRACT

There is described the resolution of the racemate S-(carboxymethyl)-(RS)-cysteine. It is carried out by means of the optical isomers of 2-amino-1-phenyl-propan-1-ol. This process makes it possible to obtain in a simple manner S-(carboxymethyl)-(R)-cysteine which is important for pharmaceutical purposes and is made from synthetically produced cysteine.

13 Claims, No Drawings

PROCESS FOR THE RESOLUTION OF THE RACEMATE S-(CARBOXYMETHYL)-(RS)-CYSTEINE (A)

BACKGROUND OF THE INVENTION

The invention is directed to a process for the resolution of the racemate S-(carboxymethyl)-(RS)-cysteine, especially for the purpose of recovery of S-(carboxymethyl)-(R)-cysteine. This substance is needed for pharmaceutical purposes and serves for example, as a mucolyticum.

It is known to produce S-(carboxymethyl)-(R)-cysteine by reacting (R)-cysteine—also called L-cysteine—with chloracetic acid in alkali medium (Armstrong, J. Org. Chem. Vol. 16(1951) pages 749 to 753).

The (R)-cysteine needed for this purpose as starting material is generally obtained from keratin containing natural materials. For this purpose these are hydrolyzed; the (RR)-cystine set free is separated and reduced to (R)-cysteine (Org. Synth. Vol. 5(1925) pages 39 to 41); German OS No. 2653332 (and related Scherberich U.S. Pat. No. 4,245,177 the entire disclosure of which is incorporated by reference and relied upon), Vigneaud, J. Amer. Chem. Soc. Vol. 52(1930) pages 4500–4504). However, suitable natural materials are only available to a limited extent.

In the synthetic production of cysteine, for example, from thiazolines-3 substituted in the 2-position via the corresponding thiazolidin-4-carbonitriles the racemate (RS)-cysteine is formed. The entire disclosure of German OS 2645748 is hereby incorporated by reference and relied upon. It is known to obtain (R)-cysteine by reacting the (RS)-cysteine with dicyandiamide to form (RS)-2-guanidine-1,3-thiazolidin-4-carboxylic acid, from this with the help of the copper complex salt of (R)-aspartic acid there is separated the (R)-2-guanidine-1,3-thiazolidin-4-carboxylic acid and subsequently there is split off from this the (R)-cysteine (German AS No. 1795021). This process is for the recovery of the (R)-cysteine thus is cumbersome and expensive, which is unsuited for use on an industrial scale.

SUMMARY OF THE INVENTION

It has now been found that the racemate S-(carboxymethyl)-(RS)-cysteine is resolved by means of the optical isomers of 2-amino-1-phenyl-propan-1-ol. While in the previous process first (R)-cysteine is obtained, in a given case through the cumbersome resolution of the racemate (RS)-cysteine, and the (R)-cysteine reacted to S-(carboxymethyl)-(R)-cysteine, rather now there is first reacted (RS)-cysteine to prepare S-(carboxymethyl)-(RS)-cysteine, and then this racemate resolved. This resolution can be carried out in a simple manner and yields the optical isomers of the S-(carboxymethyl)-cysteine in high yields in outstanding optical and chemical purity.

The S-(carboxymethyl)-(RS)-cysteine is produced from the (RS)-cysteine in the same and known manner as S-(carboxymethyl)-(R)-cysteine from the (R)-cysteine, namely for example, by conversion by means of chloroacetic acid in alkaline medium according to the process set forth in Armstrong, J. Org. Chem. Vol. 16(1951) pages 749 to 753.

According to the invention, the S-(carboxymethyl)-(R)-cysteine is separated from the racemate by means of (1R,2S)-2-Amino-1-phenyl-propan-1-ol, and the S-(carboxymethyl)-(S)-cysteine by means of (1S,2R)-2-Amino-1-phenyl-propan-1-ol. The salts formed from (1R,2S)-2-Amino-1-phenyl-propan-1-ol and S-(carboxymethyl)-(R)-cysteine as well as from (1S,2R)-2-Amino-1-phenyl-propan-1-ol and S-(carboxymethyl)-(S)-cysteine previously have not been described. The salt of (1R,2S)-2-Amino-1-phenyl-propan-1-ol and S-(carboxymethyl)-(R)-cysteine is considerably less soluble than the diastereomer salt thereto from (1R,2S)-2-Amino-1-phenyl-propan-1-ol and S-(carboxymethyl)-(S)-cysteine; the salt from (1S,2R)-2-Amino-1-phenyl-propan-1-ol and S-(carboxymethyl)-(S)-cysteine is considerably less soluble than the diastereomer salt thereto from (1S,2R)-2-Amino-1-phenyl-propan-1-ol and S-(carboxymethyl)-(R)-cysteine.

To carry out the process of the invention the procedure is as customary in the separation of a racemate. The racemate S-(carboxymethyl)-(RS)-cysteine in the presence of a solvent is brought together with the desired optical isomer of 2-Amino-1-phenyl-propan-1-ol, and then the diastereomer salts formed are separated.

The salts which are diastereomers to each other in numerous solvents show sufficiently large differences in solubility. For example, water is among these solvents. Preferably, there are used as solvents primary or secondary alkanols having up to 6 carbon atoms or ethers and among these solvents especially those which are unlimitedly miscible with water. For example, there can be used hexan-1-ol, butan-1-ol, methyl tert butyl ether and especially methanol, ethanol, propan-2-ol, dioxane and tetrahydrofurane. Other solvents include propan-1-ol, butan-2-ol, 2-methylpropan-1-ol. The solvents can also be used in mixtures with each other or in mixtures with water, but the mixtures are suitably so selected that the solvents form a single phase.

The racemate S-(carboxymethyl)-(RS)-cysteine, as well as the optical isomer concerned of the 2-amino-1-phenyl-propan-1-ol can be employed in solid form or as a suspension or solution in the solvent. The optical isomer of 2-amino-1-phenyl-propan-1-ol, and the racemate S-(carboxymethyl)-(RS)-cysteine can be employed in any desired proportion to each other. However, generally it is suitable to employ per mole of the racemate not less than about 0.5 and not more than about 5.0 moles of the optical isomer. Preferably, per mole of the racemate, there is used 0.9 to 1.1, especially 1.0 mole of the optical isomer. There can be employed all temperatures at which the solvent is present in liquid form.

For resolution of the diastereomer salts, the preferred procedure is by a fractional crystallization in the customary manner. The mixture is brought to elevated temperatures, preferably to temperatures near the boiling point, so much solvent used that all materials are dissolved, and subsequently the solution cooled for the crystallization.

The concerned S-(carboxymethyl)-cysteine is set free from the precipitated salts from S-(carboxymethyl)-(R)-cysteine, and (1R,2S)-2-amino-1-phenyl-propan-1-ol or S-(carboxymethyl)-(S)-cysteine and (1S,2R)-2-amino-1-phenyl-propan-1-ol by treating the salts with strong acids, preferably strong mineral acids, such as hydrochloric acid. Other mineral acids include hydrobromic acid and sulfuric acid.

Unless otherwise indicated, all parts and percentages are by weight.

The compositions can comprise, consist essentially of or consist of the stated materials and the process can comprise, consist essentially of or consist of the steps set forth with the stated materials.

DETAILED DESCRIPTION

EXAMPLES

The optically active materials obtained in each case were examined as to their specific rotation $[\alpha]_D^{20}$. This is given in degrees .cm$^3$/dm.g. Percent data are weight percents.

A. Production of S-(carboxymethyl)-(RS)-Cysteine

As starting material, there served (RS)-cysteine hydrochloride which was produced by the process of German OS No. 2645748. 140 grams (1 mole) of this material together with 160 grams (4 moles) of sodium hydroxide were dissolved in 1000 ml of water. To this solution there was first added 3 grams of sodium hydrogen sulfide and then in the course of 45 minutes 95 grams (1 mole) of monochloroacetic acid. The temperature of the mixture in the meanwhile was held at 20° C., and after that held for 3 hours at 20° to 30° C., the reaction mixture was subsequently adjusted to a pH of 3.0 by addition of concentrated, aqueous hydrochloric acid. Hereby, the S-(carboxymethyl)-(RS)-cysteine separated out. It was filtered off at 10° C., and washed with water until it was free from chloride ions. Then, it was dried under reduced pressure at 105° C. The yield was 173 grams, corresponding to 97% based on the cysteine hydrochloride employed. The melting point (decomposition point) of the S-(carboxymethyl)-(RS)-cysteine was 188° to 192° C.

B. Resolution of the Racemate

S-(Carboxymethyl)-(RS)-Cysteine

EXAMPLE 1

50.0 grams (0.28 mole) of the racemate S-(carboxymethyl)-(RS)-cysteine obtained according to process A were suspended in 400 ml of methanol which contained 10% water. To this suspension in the course of one hour, there were added 42.5 grams (0.28 mole) of (1R,2S)-2-amino-1-phenyl-propan-1-ol. The mixture meanwhile was heated to 40° to 50° C. and held for a further 30 minutes under reflux at the boiling point, then slowly cooled to 30° C. and filtered. The residue was washed with 200 ml of anhydrous methanol, and dried at 50° C. and 25 mbar. The material recovered was the salt of S-(carboxymethyl)-(R)-cysteine and (1R,2S)-2-amino-1-phenyl-propan-1-ol. The yield was 41.6 grams, corresponding to 90% based on the S-(carboxymethyl)-(R)-cysteine contained in the racemate employed. The melting point of the salt recovered was 68° C. and the specific rotation −38.3° (c=1 in water).

The salt was dissolved in 150 ml of water and the solution adjusted to pH 3.0 by means of 2 N aqueous hydrochloric acid at 25° C. Hereby, the S-(carboxymethyl)-(R)-cysteine was precipitated. It was filtered off, washed with 100 ml of cold water and then dried at 105° C. and 25 mbar. The yield was 21.7 grams, corresponding to 96% based on the salt employed. The melting point (decomposition point) of the S-(carboxymethyl)-(R)-cysteine was 190° to 192° C., and the specific rotation −34.5° (c=10 in aqueous sodium hydroxide solution, pH 6.0).

The filtrate remaining in the filtering off of the S-(carboxymethyl)-(R)-cysteine was treated with 200 ml of a 50% aqueous sodium hydroxide solution. The mixture was extracted three times, each time with 100 ml of methylene chloride. The combined extracts were dried with sodium sulfate. Then the methylene chloride was driven off and the residue recrystallized in methyl tert. butyl ether. There were obtained 18.6 grams of (1R,2S)-2-amino-1-phenyl-propan-1-ol.

The filtrate remaining after filtering off the salt of S-(carboxymethyl)-(R)-cysteine and (1R,2S)-2-amino-1-phenyl-propan-1-ol was evaporated to dryness. The residue was taken up in 200 ml of water and the mixture adjusted to pH 3.0 with 2 N aqueous hydrochloric acid. Hereby, there was precipitated S-(carboxymethyl)-(S)-cysteine with a small amount of S-(carboxymethyl)-(R)-cysteine. The material was filtered off, then first heated in a mixture of acetic acid and acetic anhydride and after driving off the acetic acid treated with hydrochloric acid. Hereby, there was obtained racemic S-(carboxymethyl)-cysteine.

The filtrate remaining after filtering off the S-(carboxymethyl)-(S)-cysteine was treated with 200 ml of 50% aqueous sodium hydroxide solution. The mixture was extracted three times, each time with 100 ml of methylene chloride. The combined extracts were dried with sodium sulfate. Then, the methylene chloride was driven off and the residue recrystallized in methyl tert. butyl ether. There were obtained hereby, 23.1 grams of (1R,2S)-2-amino-1-phenyl-propan-1-ol. Thus, there were recovered altogether 41.7 grams, corresponding to 98% of the (1R,2S)-2-amino-1-phenyl-propan-1-ol employed.

EXAMPLE 2

The procedure was as in Example B1, but the starting materials were suspended in 1000 ml of water free methanol, and the suspension was held for 2 hours under stirring at 50° C. to 60° C. There were obtained 37.0 grams, corresponding to 80% yield of the salt of S-(carboxymethyl)-(R)-cysteine and (1R,2S)-2-amino-1-phenyl-propan-1-ol. The melting point of the salt was 68° C. and the rotation −38.3° (c=1 in water). From this salt there was recovered in accordance with Example B 1 S-(carboxymethyl)-(R)-cysteine. The yield was 19.3 grams, corresponding to 96%. The melting point (decomposition point) was 188° to 191° C. and the rotation −34.0° (c=1 in aqueous sodium hydroxide, pH=6.0).

The filtrate remaining after filtering off the salt of S-(carboxymethyl)-(R)-cysteine and (1R,2S)-2-amino-1-phenyl-propan-1-ol was adjusted to pH 3.0 with 2 N aqueous hydrochloric acid. The material precipitated hereby was filtered off, washed with cold water and dried at 105° C. and 25 mbar. It consisted of 79% of S-(carboxymethyl)-(S)-cysteine and up to 21% of S-(carboxymethyl)-(R)-cysteine. There were obtained 26.8 grams, corresponding to 53.6% based on the S-(carboxymethyl)-(RS)-cysteine. The rotation of the material was +20.0° (c=10 in aqueous sodium hydroxide solution pH=6.0).

EXAMPLE 3

The procedure was as in Example B1, but the S-(carboxymethyl)-(RS)-cysteine was suspended in 1000 ml of water free methanol. There were obtained 37.0 grams, corresponding to an 80% yield of the salt of S-(carboxymethyl)-(R)-cysteine and (1R,2S)-2-amino-1-phenyl-propan-1-ol. The melting point of the salt was 68° C. and the rotation −37.5° (c=1 in water). Elemental analysis: C=50,79% (50,89%); H=6,80% (6,71%); N=8,47% (8,48%); S=9,78% (9,71%), (In parantheses calculated for $C_{14}H_{22}N_2O_5S$).

EXAMPLE 4

The procedure was as in Example B1, but the starting materials were suspended in dioxane, and there was supplied water to this suspension at the boiling point until all materials were dissolved. The solution was cooled in the course of 2 hours to 25° C. There were obtained 36.0 grams, corresponding to 78% yield of the salt of S-(carboxymethyl)-(R)-cysteine and (1R,2S)-2-amino-1-phenyl-propan-1-ol. The melting point was 68° C. and the rotation −37.4° (c=1 in water).

EXAMPLE 5

The procedure was as in Example B4, but in place of the dioxane there were employed 800 ml of propan-2-ol. The yield was 43.9 grams, corresponding to 95%. The melting point was 67° C. and the rotation −38.0° (c=1 in water).

EXAMPLE 6

The procedure was as in Example B4, but instead of the dioxane there were employed 200 ml of tetrahydrofurane. The yield was 54.5 grams, corresponding to 96%. The melting point was 67° C. and the rotation −38.4° (c=1 in water).

EXAMPLE 7

The procedure was as in Example B1, except the S-(carboxymethyl)-(RS)-cysteine was suspended in 100 ml of water, to this suspension there was added the (1R,2S)-2-amino-1-phenyl-propan-1-ol, the suspension warmed to 60° C. and evaporated under reduced pressure to 105 grams and the residue taken up in 800 ml of boiling methanol. There were obtained 37.4 grams, corresponding to 81% yield, of the salt of S-(carboxymethyl)-(R)-cysteine and (1R,2S)-2-amino-1-phenyl-propan-1-ol. The melting point was 68° C. and the rotation −38.1° (c=1 in water).

EXAMPLE 8

The procedure was as in Example B7, but instead of methanol there was employed 800 ml of ethanol. The yield was 37.0 grams, corresponding to 80%. The melting point was 67° C. and the rotation −37.8° (c=1 in water).

EXAMPLE 9

The procedure was as in Example B2, except there were employed 100 grams (0.56 mole) of S-(carboxymethyl)-(RS)-cysteine and 124 grams (0.82 mole) of (1R,2S)-2-amino-1-phenyl-propan-1-ol in 800 ml of methanol which contained 2% of water, the mixture was held under reflux at the boiling temperature for one hour, and then cooled to 30° C. in the course of 30 minutes. There was obtained 89.0 grams, corresponding to 96%, of the salt of S-(carboxymethyl)-(R)-cysteine and (1R,2S)-2-amino-1-phenyl-propan-1-ol. The melting point of the salt was 67° C. and the rotation −37.4° (c=1 in water).

EXAMPLE 10

The procedure was as in Example B1 except in place of (1R,2S)-2-amino-1-phenyl-propan-1-ol there were employed 42.5 grams (0.28 mole) of (1S, 2R)-2-amino-1-phenyl-propan-1-ol. There was obtained the salt of the S-(carboxymethyl)-(S)-cysteine and (1S,2R)-2-amino-1-phenyl-propan-1-ol. The yield was 39.3 grams, corresponding to 85% based on the S-(carboxymethyl)-(S)-cysteine contained in the racemate employed. Elemental analysis: C=50.97% (50.89%); H=6.70% (6.71%); N=8.25% (8.48%); S=9.88% (9.71%), (In parantheses calculated for $C_{14}H_{22}N_2O_5S$).

The S-(carboxymethyl)-(S)-cysteine was set free from the salt obtained by the process of Example B1. The yield was 20.4 grams, corresponding to 96% based on the salt employed. The melting point (decomposition-point) of the S-(carboxymethyl)-(S)-cysteine was 189° to 191° C. and the rotation +34.2° (c=10 in aqueous sodium hydroxide solution, pH 6.0).

The entire disclosure of German priority application P 3134042.3 is hereby incorporated by reference.

What is claimed is:

1. A process of resolving the racemate S-(carboxymethyl)-(RS)-cysteine comprising dissolving the racemate together with an optical isomer of 2-amino-1-phenyl-propan-1-ol in a solvent in which the salt of said optical isomer with one of the isomer present in said racemate is less soluble than the salt of said optical isomer with the other one of the isomers present in said racemate and precipitating the less soluble salt.

2. A process according to claim 1, wherein the solvent is water, a primary or secondary alkanol having 1 to 6 carbon atoms, an ether, or a mixture of such solvents.

3. A process according to claim 2, wherein the solvent is methanol, ethanol, propan-2-ol, dioxane or tetrahydrofurane, or a mixture of such solvent with a minor amount of water.

4. A process according to claim 3, wherein the solvent is anhydrous.

5. A process according to claim 3, wherein the solvent contains a minor amount of water.

6. A process according to claim 2, wherein the solvent comprises an alkanol having 1 to 6 carbon atoms.

7. A process according to claim 2, wherein the solvent comprises methyl tert butyl ether, dioxane, or tetrahydrofurane.

8. A process according to claim 3, wherein the solvent comprises methanol, ethanol, or propan-1-ol.

9. A compound which is either (1) a salt of S-(carboxymethyl)-(R)-cysteine and (1R,2S)-2 amino-1-phenyl-propan-1-ol or (2) a salt of S-(carboxymethyl)-(S)-cysteine and (1S,2R)-2-amino-1-phenyl-propan-1-ol.

10. A compound according to claim 9, which is a salt of S-(carboxymethyl)-(R)-cysteine and (1R,2S)-2-amino-1-phenyl-propan-1-ol.

11. A composition comprising the compound of claim 10, substantially free from the salt of S-(carboxymethyl)-(S)-cysteine and (1R,2S)-2-amino-1-phenyl-propan-1-ol.

12. A compound according to claim 9, which is a salt of S-(carboxymethyl)-(S)-cysteine and (1S,2R)-2-amino-1-phenyl-propan-1-ol.

13. A composition comprising the compound of claim 12, substantially free from the salt of S-(carboxymethyl)-(R)-cysteine and (1S,2R)-2-amino-1-phenyl-propan-1-ol.

* * * * *